US00PP09848P

United States Patent [19]

Meier et al.

[11] Patent Number: Plant 9,848

[45] Date of Patent: Apr. 1, 1997

[54] 'BA-74-114' KENTUCKY BLUEGRASS

[75] Inventors: Virgil D. Meier; Eugene W. Mayer, both of Marysville, Ohio

[73] Assignee: OMS Investments, Inc., Wilmington, Del.

[21] Appl. No.: 532,995

[22] Filed: Sep. 25, 1995

[51] Int. Cl.[6] ..... A01H 5/00

[52] U.S. Cl. ..... Plt./90.2

[58] Field of Search ..... Plt./90.2

[56] References Cited

U.S. PATENT DOCUMENTS

| | | | |
|---|---|---|---|
| P.P. 3,156 | 7/1970 | Fuchigami et al. | Plt./90.2 |
| P.P. 3,186 | 5/1972 | Barenbrug et al. | Plt./90.2 |
| P.P. 4,336 | 11/1978 | Mayer et al. | Plt./90.2 |
| P.P. 6,280 | 9/1988 | Meier et al. | Plt./90.2 |
| P.P. 6,537 | 1/1989 | Meier et al. | Plt./90.2 |
| P.P. 6,538 | 1/1989 | Meier et al. | Plt./90.2 |
| P.P. 6,585 | 2/1989 | Meier et al. | Plt./90.2 |
| P.P. 7,831 | 3/1992 | Meier et al. | Plt./90.2 |
| P.P. 8,490 | 12/1993 | Meier et al. | Plt./90.2 |
| P.P. 9,036 | 1/1995 | Meier et al. | Plt./90.2 |
| P.P. 9,209 | 7/1995 | Meier et al. | Plt./90.2 |

*Primary Examiner*—James R. Feyrer
*Attorney, Agent, or Firm*—Jones, Day, Reavis & Pogue

[57] ABSTRACT

A variety of Kentucky Bluegrass having a medium to high level of resistance to leaf spot and melting out disease, dollar spot, rusts, stripe smut and powdery mildew; a dark green color throughout the growing season; the ability to form medium to high quality turf under a wide variety of environmental conditions; a moderately wide blade; a low growth habit; and a medium level of seed yielding capacity.

1 Drawing Sheet

BACKGROUND OF THE INVENTION

1. Field of the Invention

The present invention relates to a new and distinct variety of *Poa pretensis* that has been designated Ba 74-114 Kentucky Bluegrass.

2. Description of Related Art

Kentucky bluegrasses have been disclosed in U.S. Pat. No. P.P. 3,156, issued May 9, 1972; U.S. Pat. No. P.P. 3,186, issued May 23, 1972; U.S. Pat. No. P.P. 4,336, issued Nov. 28, 1978; U.S. Pat. No. P.P. 6,280, issued Sep. 6, 1988; U.S. Pat. Nos. P.P. 6,537 and 6,538, issued on Jan. 17, 1989; U.S. Pat. No. P.P. 6,585, issued Feb. 7, 1989; U.S. Pat. No. P.P. 7,831, issued Mar. 17, 1992; U.S. Pat. No. P.P. 8,490, issued Dec. 7, 1993; U.S. Pat. No. P.P. 9,036, issued Jan. 3, 1995; U.S. Pat. No. P.P. 9,209, issued Jul. 18, 1995; and pending U.S. Plant patent application Ser. No. 08/453,864, filed May 30, 1995.

SUMMARY OF THE VARIETY

Ba 74-114 plant material originated by crossing a Vantage Kentucky bluegrass plant as the seed parent with an Anheuser Dwarf Kentucky bluegrass plant as the pollen parent. As a result of this breeding, a distinct variety was produced and asexually propagated by rhizomes, tillers and disseminules.

Seed of Ba 74-114 Kentucky Bluegrass was produced first at Marysville, Ohio and later at Gervais, Oreg. This seed was used to plant turf performance evaluation trials and later seed production fields. Asexual production of Ba 74-114 by propagules (tillers and rhizomes) and by disseminules (modified caryopses produced by apomixis) has consistently produced progeny plants indistinguishable from the mother plant. The apomixis level of Ba74-114 is approximately 95% based upon examining seedling characteristics of approximately 100 to 150 seedlings from different crop years in a growth chamber.

Ba 74-114 has a number of highly desirable characteristics including a medium to high level of resistance to Drechslera spp. that causes leaf spot, melting out and crown rot; *Scherotinia homoeocarpa* that causes dollar spot; Puccinia spp. that causes several types of rust infections; *Erysiphe graminis* that causes powdery mildew and *Ustilago striiformis* that causes stripe smut. Ba 74-114 has an attractive leafy turf type, low growth habit; moderately wide leaf blades and an attractive dark green color which can be maintained throughout the entire growing season. Ba 74-114 demonstrates strong early spring greening and good winter color under mild winter conditions.

Ba 74-114 is an overall good turfgrass performer as evidenced by medium to high scores for quality and color. Ba 74-114 has a medium seed yield potential in the bluegrass seed production region of the northwestern U.S.

In comparison with a number of other Kentucky bluegrasses, Ba 74-114 has a significantly longer seed and rachilla than many other grasses and a below average seed count. The panicle is significantly longer than many other grasses, below average in width and whorl number and a significantly lower branch count. Ba 74-114 has significantly larger spikelets, longer glumes and above average number of florets. Its culm and internode are significantly longer than many other grasses. The peduncle is slightly above average in length and width. It has a flag leaf that is above average in length and width and significantly thicker than many other grasses. The vegetative leaf is below average in length but it is a significantly wider leaf than most other grasses and significantly thicker than many other grasses. The ligule of the vegetative leaf is significantly shorter and sheath color is significantly greater than many other grasses.

Ba 74-114 Kentucky Bluegrass is lower growing, darker green in color and substantially more resistant to leaf spot disease than Vantage Kentucky Bluegrass, its seed parent. Ba 74-114 is a higher seed yielder and a more vigorous plant than Anheuser Kentucky Bluegrass, its pollen parent.

DETAILED DESCRIPTION OF THE VARIETY

Figure 1:
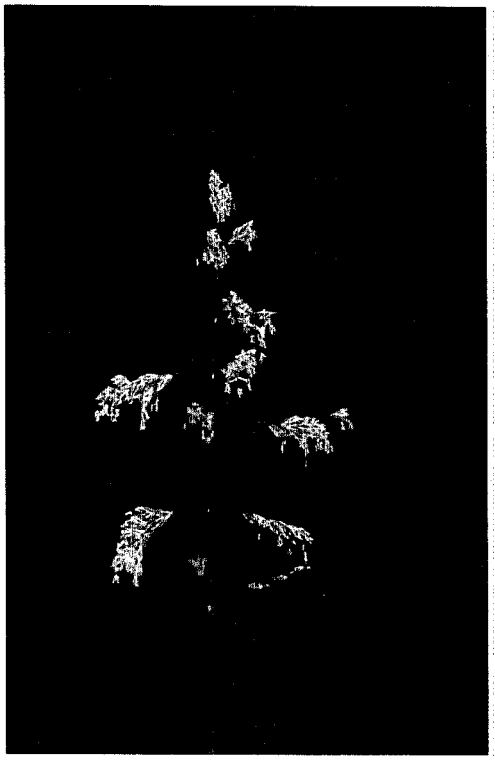
FIG. 1 is a Ba 74-114 Kentucky Bluegrass panicle.
Figure 2:
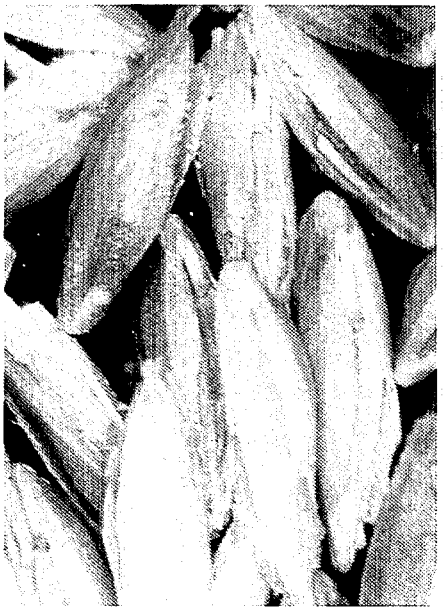
FIG. 2 is a Ba 74-114 Kentucky Bluegrass seed.
Figure 3:
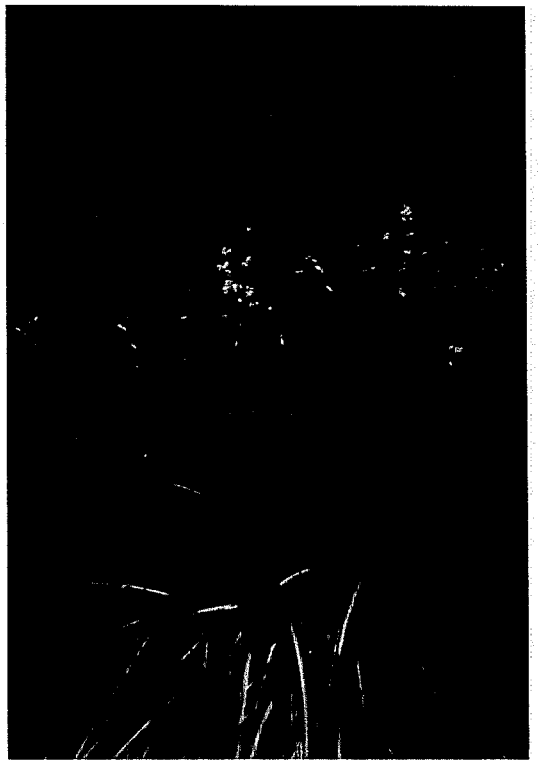
FIG. 3 is a Ba 74-114 Kentucky Bluegrass plant shortly after completing anthesis.

BA 74-114 Kentucky Bluegrass (*Poa pratensis* L.) is perennial with creeping rhizomes forming a dense turf. When plants overwinter in the field under freezing temperatures and are then brought into the greenhouse during later winter to continue growth undisturbed by clipping under moderate temperatures (60°–80° F.), culms are erect averaging 44.9 cm in length and 3.7 nodes per culm and the uppermost internode averages 13.4 cm in length. The peduncle averages 24.7 cm in length and 0.71 mm in width. The vegetative leaf averages 18.9 cm in length, 4.5 mm in width and 0.36 mm in thickness and the ligule 0.14 mm in length. The flag leaf averages 5.3 cm in length, 3.4 mm in width, 0.23 mm in thickness and a ligule length of 1.2 mm.

The panicle averages 88.8 mm in length, 52.0 mm in width, and 9.3 whorls. Both the lowest whorl and the third whorl from the bottom of the panicle average 2.1 branches. A spikelet in the lowest whorl averages 5.6 mm in length, 3.2 mm in width, 4.1 florets and the outer glume and inner glume average 3.5 and 3.9 mm in length, respectively. A spikelet from the third whorl from the bottom of the panicle averages 5.6 mm in length, 3.3 mm in width, 4.1 florets, and the outer glume and inner glume averages 3.3 and 3.8 mm in length, respectively.

After the seed has been conditioned, the lemma has a generally smooth keel with occasional short hairs and a few long fine hairs at the base. Conditioned seed of Ba 74-114 averages 3.23 mm in length, 0.89 mm in width, a rachilla length of 0.88 mm, and, contains an average quantity of lemma hairs. The seed count for Ba 74-114 averages approximately 978,000 seeds per pound.

Comparisons of Ba 74-114 with other Kentucky Bluegrass varieties in terms of seed dimension and seed numbers per pound are shown in Tables 1 and 2 as follows:

TABLE 1

Morphological Comparison of Seed and Rachilla Measurements and Lemma Hair of Ba 74-114 and Other Kentucky Bluegrass Varieties at Marysville, OH After Conditioning

| | Seed | | | |
|---|---|---|---|---|
| Variety | Length mm | Width mm | Rachilla mm | Lemma* Hair |
| Ba 74-114 | 3.23 | 0.89 | 0.88 | 4.2 |
| Ba73-366 | 3.04 | 0.91 | 0.80 | 4.4 |
| Ba73-381 | 3.00 | 0.94 | 0.86 | 4.9 |
| Abbey | 2.97 | 0.89 | 0.80 | 3.8 |
| Adelphi | 2.70 | 0.84 | 0.65 | 4.4 |
| America | 2.40 | 0.68 | 0.68 | 2.8 |
| Baron | 3.08 | 0.81 | 0.71 | 5.0 |
| Bristol | 2.94 | 0.88 | 0.73 | 4.3 |
| Chateau | 2.81 | 0.86 | 0.71 | 4.5 |
| Coventry | 2.71 | 0.81 | 0.70 | 4.0 |
| Eclipse | 2.77 | 0.83 | 0.68 | 3.5 |
| Georgetown | 2.94 | 0.82 | 0.74 | 4.9 |
| Gnome | 2.78 | 0.83 | 0.75 | 4.1 |
| Kelly | 3.07 | 0.89 | 0.75 | 4.2 |
| Marquis | 2.97 | 0.87 | 0.83 | 4.7 |
| Midnight | 2.94 | 0.76 | 0.78 | 5.7 |
| Nassau | 3.07 | 0.86 | 0.68 | 3.4 |
| Ram I | 3.23 | 0.89 | 0.80 | 6.0 |
| Touchdown | 2.93 | 0.88 | 0.71 | 4.6 |
| Victa | 3.00 | 0.80 | 0.82 | 3.5 |
| LSD (.05) | 0.16 | 0.05 | 0.13 | 0.86 |

*Rating Scale: 0–9; 9 = longest row of hairs

TABLE 2

Comparison of Seed Numbers Per Pound of Ba 74-114 and Other Kentucky Bluegrass Varieties at Marysville, OH After Conditioning

| Variety | Seeds Per Pound |
|---|---|
| Ba 74-114 | 978,000 |
| Ba73-366 | 1,025,586 |
| Ba73-381 | 1,171,000 |
| Abbey | 1,003,037 |
| Adelphi | 1,383,976 |
| America | 1,659,824 |
| Baron | 1,051,693 |
| Bristol | 1,270,821 |
| Chateau | 1,300,105 |
| Coventry | 1,246,200 |
| Eclipse | 1,335,668 |
| Georgetown | 1,431,000 |
| Gnome | 1,017,641 |
| Kelly | 921,166 |
| Marquis | 1,054,642 |
| Midnight | 1,227,000 |
| Nassau | 1,127,130 |
| Ram I | 1,214,000 |
| Touchdown | 1,211,000 |
| Victa | 1,038,298 |

Ba 74-114 differs significantly morphologically from many other Kentucky Bluegrass varieties in regard to the following characteristics: (1) seed length; (2) rachilla length; (3) panicle length; (4) number of branches in the whorl; (5) spikelet length and width; (6) glume length and width; (7) culm length and internode length; (8) flag leaf thickness; and (9) vegetative leaf width and sheath color.

Since environmental conditions such as soil and climate may influence morphological characteristics to some extent, comparisons of morphological characteristics of Ba 74-114 were made with other Kentucky Bluegrass varieties and the comparisons are set forth in the following Tables 3–8:

TABLE 3

Morphological Comparison of Panicles, Whorl Number and Whorl Branches of Ba 74-114 and Other Kentucky Bluegrass Varieties in the Greenhouse at Marysville, OH

| | Panicles | | | | Number of Branches | |
|---|---|---|---|---|---|---|
| Variety | Nodding* | Length mm | Width mm | Whorl Number | Lowest Whorl | Third Whorl |
| Ba 74-114 | 2.0 | 88.8 | 62.0 | 9.3 | 2.1 | 2.1 |
| Ba73-366 | 1.6 | 88.8 | 68.4 | 8.8 | 4.3 | 3.7 |
| Ba73-381 | 1.1 | 80.2 | 55.3 | 9.8 | 4.1 | 3.9 |
| Abbey | 1.6 | 80.4 | 59.3 | 9.3 | 3.8 | 3.3 |
| Adelphi | 1.8 | 106.8 | 76.4 | 10.0 | 3.6 | 3.0 |
| America | 2.3 | 67.7 | 51.1 | 8.8 | 3.3 | 3.5 |
| Baron | 2.2 | 92.6 | 71.0 | 10.0 | 3.4 | 2.8 |
| Bristol | 2.0 | 85.5 | 61.5 | 8.4 | 2.8 | 2.7 |
| Chateau | 2.9 | 65.2 | 57.3 | 8.5 | 3.3 | 2.8 |
| Coventry | 2.5 | 64.0 | 54.2 | 8.4 | 3.3 | 2.5 |
| Eclipse | 1.3 | 89.2 | 74.0 | 10.7 | 3.3 | 2.1 |
| George-town | 1.0 | 80.0 | 57.0 | 7.4 | 2.1 | 2.6 |
| Gnome | 1.1 | 80.6 | 56.0 | 10.6 | 4.6 | 3.9 |
| Kelly | 2.0 | 88.0 | 70.2 | 9.8 | 4.6 | 3.7 |
| Marquis | 1.1 | 82.0 | 63.0 | 10.3 | 3.9 | 3.6 |
| Midnight | 2.0 | 75.8 | 48.4 | 7.1 | 2.9 | 3.0 |
| Nassau | 2.2 | 91.2 | 68.6 | 10.0 | 2.5 | 2.1 |
| Ram I | 1.3 | 67.7 | 47.0 | 7.3 | 3.0 | 3.2 |
| Touchdown | 1.1 | 73.1 | 75.0 | 7.6 | 2.1 | 2.3 |
| LSD (.05) | 0.68 | 7.35 | 8.62 | 0.66 | 0.72 | 0.50 |

*Rate Scale: 1–9; 9 = most nodding

TABLE 4

Morphological Comparison of Spikelets and Florets of Ba 74-114 and Other Kentucky Bluegrass Varieties in the Greenhouse at Marysville, OH

| | Spikelet* | | | | Number of Florets Per Spikelet | |
|---|---|---|---|---|---|---|
| | Lowest Whorl | | Third Whorl | | | |
| Variety | Length mm | Width mm | Length mm | Width mm | Lowest Whorl | Third Whorl |
| Ba 74-114 | 5.6 | 3.2 | 5.6 | 3.3 | 4.1 | 4.1 |
| Ba73-366 | 4.6 | 2.5 | 4.7 | 2.6 | 2.6 | 2.8 |
| Ba73-381 | 4.7 | 2.4 | 4.6 | 2.6 | 2.7 | 2.7 |
| Abbey | 4.4 | 2.2 | 4.5 | 2.2 | 3.0 | 3.0 |
| Adelphi | 4.6 | 2.2 | 4.8 | 2.2 | 4.4 | 4.4 |
| America | 4.6 | 2.2 | 4.4 | 2.3 | 4.5 | 4.3 |
| Baron | 5.4 | 2.8 | 5.4 | 3.1 | 4.0 | 4.2 |
| Bristol | 4.9 | 2.4 | 5.0 | 2.5 | 4.2 | 4.5 |
| Chateau | 4.4 | 2.4 | 4.4 | 2.4 | 3.4 | 3.5 |
| Coventry | 4.4 | 2.2 | 4.5 | 2.4 | 3.2 | 3.5 |
| Eclipse | 4.6 | 2.4 | 4.6 | 2.4 | 3.6 | 3.6 |
| Georgetown | 5.0 | 2.3 | 5.0 | 2.6 | 4.8 | 4.9 |
| Gnome | 4.6 | 2.5 | 4.6 | 2.9 | 3.2 | 3.2 |
| Kelly | 5.1 | 2.5 | 5.2 | 2.8 | 3.7 | 3.8 |
| Marquis | 4.3 | 2.2 | 4.4 | 2.3 | 3.1 | 2.9 |
| Midnight | 5.3 | 2.5 | 5.5 | 2.4 | 4.4 | 4.7 |
| Nassau | 4.7 | 2.6 | 4.8 | 3.0 | 4.2 | 4.3 |
| Ram I | 5.4 | 2.6 | 5.3 | 2.8 | 3.6 | 3.4 |
| Touchdown | 5.1 | 2.9 | 4.8 | 2.8 | 4.1 | 4.0 |
| Victa | 4.5 | 2.5 | 4.5 | 2.4 | 3.3 | 3.2 |
| LSD (.05) | 0.41 | 0.35 | 0.38 | 0.35 | 0.58 | 0.53 |

*Microscope measurements

TABLE 5

Morphological Comparison of Glumes of Ba 74-114 and Other Kentucky Bluegrass Varieties in the Greenhouse at Marysville, OH

| | Glume Length (mm) | | | |
|---|---|---|---|---|
| | Outer | | Inner | |
| Variety | Lowest Whorl | Third Whorl | Lowest Whorl | Third Whorl |
| Ba 74-114 | 3.5 | 3.3 | 3.9 | 3.8 |
| Ba73-366 | 2.8 | 2.8 | 3.2 | 3.1 |
| Ba73-381 | 2.8 | 2.9 | 3.2 | 3.1 |
| Abbey | 2.7 | 2.7 | 3.1 | 3.1 |
| Adelphi | 2.7 | 2.6 | 3.0 | 3.1 |
| America | 2.1 | 2.1 | 2.5 | 2.5 |
| Baron | 3.1 | 3.2 | 3.6 | 3.7 |
| Bristol | 2.8 | 3.0 | 3.3 | 3.4 |
| Chateau | 2.8 | 2.9 | 3.1 | 3.2 |
| Coventry | 2.7 | 2.8 | 3.1 | 3.1 |
| Eclipse | 3.0 | 3.0 | 3.4 | 3.4 |
| Georgetown | 2.8 | 2.8 | 3.1 | 3.1 |
| Gnome | 2.8 | 2.9 | 3.3 | 3.3 |
| Kelly | 3.0 | 3.1 | 3.4 | 3.5 |
| Marquis | 2.8 | 2.7 | 3.1 | 3.1 |
| Midnight | 2.6 | 2.6 | 3.0 | 3.1 |
| Nassau | 2.6 | 2.7 | 2.9 | 3.0 |
| Ram I | 2.9 | 3.0 | 3.6 | 3.5 |
| Touchdown | 3.3 | 3.3 | 3.8 | 3.8 |
| Victa | 2.8 | 2.7 | 3.1 | 3.1 |
| LSD (.05) | 0.23 | 0.22 | 0.22 | 0.23 |

TABLE 5-continued

Morphological Comparison of Glumes of Ba 74-114 and Other Kentucky Bluegrass Varieties in the Greenhouse at Marysville, OH

| | Glume Hairs* | | | |
|---|---|---|---|---|
| | Lowest Whorl | | Third Whorl | |
| Variety | Outer | Inner | Outer | Inner |
| Ba 74-114 | 2.6 | 3.2 | 2.2 | 2.8 |
| Ba73-366 | 1.7 | 1.3 | 1.3 | 2.0 |
| Ba73-381 | 1.7 | 2.3 | 2.1 | 2.3 |
| Abbey | 0.6 | 0.9 | 1.0 | 1.0 |
| Adelphi | 0.6 | 2.7 | 1.1 | 1.9 |
| America | 0.2 | 0.5 | 0.3 | 0.3 |
| Baron | 4.8 | 4.4 | 4.2 | 4.6 |
| Bristol | 1.0 | 2.2 | 0.8 | 2.2 |
| Chateau | 1.5 | 2.6 | 2.0 | 1.8 |
| Coventry | 1.5 | 2.7 | 1.6 | 2.4 |
| Eclipse | 1.5 | 1.9 | 1.8 | 1.9 |
| Georgetown | 1.7 | 2.7 | 1.2 | 2.4 |
| Gnome | 1.0 | 1.9 | 1.2 | 1.6 |
| Kelly | 1.3 | 1.5 | 1.1 | 0.8 |
| Marquis | 0.9 | 1.1 | 1.7 | 1.8 |
| Midnight | 1.8 | 2.8 | 1.0 | 2.4 |
| Nassau | 2.1 | 2.6 | 4.2 | 4.4 |
| Ram I | 1.1 | 2.3 | 0.7 | 1.2 |
| Touchdown | 0.7 | 2.1 | 1.1 | 1.4 |
| Victa | 0.8 | 1.1 | 1.1 | 1.3 |
| LSD (.05) | 0.9 | 0.9 | 0.9 | 0.9 |

*Rating Scale: 0–9; 9 = most hairs

TABLE 6

Morphological Comparison of Flag Leaves of Ba 74-114 and Other Kentucky Bluegrass Varieties in the Greenhouse at Marysville, OH

| Variety | Length cm | Width mm | Thickness mm | Angle[1/] | Curve[2/] |
|---|---|---|---|---|---|
| Ba 74-114 | 5.3 | 3.4 | 0.23 | 1.4 | 5.0 |
| Ba73-366 | 4.5 | 3.6 | 0.18 | 5.1 | 4.4 |
| Ba73-381 | 4.3 | 3.5 | 0.22 | 1.9 | 5.0 |
| Abbey | 3.8 | 3.4 | 0.14 | 2.7 | 4.1 |
| Adelphi | 5.7 | 3.4 | 0.18 | 5.2 | 5.0 |
| America | 4.3 | 2.6 | 0.21 | 4.6 | 5.0 |
| Baron | 7.0 | 4.2 | 0.15 | 9.2 | 4.4 |
| Bristol | 4.3 | 3.2 | 0.21 | 2.3 | 5.0 |
| Chateau | 4.0 | 2.7 | 0.19 | 3.4 | 2.0 |
| Coventry | 3.7 | 3.0 | 0.14 | 0.7 | 4.3 |
| Eclipse | 3.9 | 3.2 | 0.19 | 8.7 | 5.0 |
| Georgetown | 5.7 | 2.8 | 0.22 | 1.9 | 5.0 |
| Gnome | 4.5 | 3.5 | 0.18 | 4.3 | 5.0 |
| Kelly | 4.8 | 4.1 | 0.18 | 3.1 | 4.4 |
| Marquis | 5.5 | 3.6 | 0.24 | 2.7 | 4.6 |
| Midnight | 3.8 | 2.6 | 0.19 | 1.1 | 5.0 |
| Nassau | 6.0 | 3.7 | 0.19 | 5.9 | 4.7 |
| Ram I | 3.4 | 3.1 | 0.19 | 1.0 | 4.8 |
| Touchdown | 4.1 | 2.7 | 0.16 | 3.4 | 4.1 |
| Victa | 3.9 | 3.7 | 0.27 | 2.1 | 4.6 |
| LSD (.05) | 1.0 | 0.4 | 0.02 | 2.5 | 0.4 |

| | | Hairs[3/] | | |
|---|---|---|---|---|
| Variety | Ligule mm | Leaf Margin | Ligule | Sheath Color[4/] |
| Ba 74-114 | 1.2 | 0.5 | 2.1 | 1.8 |
| Ba73-366 | 1.5 | 0.4 | 2.2 | 0.5 |
| Ba73-381 | 1.3 | 0.4 | 3.6 | 1.5 |
| Abbey | 1.3 | 0.8 | 1.6 | 0.2 |
| Adelphi | 1.1 | 1.8 | 1.6 | 0.4 |
| America | 0.6 | 0.4 | 0.7 | 1.9 |
| Baron | 1.2 | 1.0 | 3.8 | 2.6 |
| Bristol | 0.6 | 0.4 | 1.9 | 2.0 |

TABLE 6-continued

Morphological Comparison of Flag Leaves of Ba 74-114 and Other Kentucky Bluegrass Varieties in the Greenhouse at Marysville, OH

| | | | | |
|---|---|---|---|---|
| Chateau | 0.9 | 1.1 | 3.1 | 0.3 |
| Coventry | 0.9 | 0.8 | 1.7 | 2.0 |
| Eclipse | 1.1 | 1.0 | 1.0 | 0.2 |
| Georgetown | 0.6 | 0.6 | 2.0 | 2.0 |
| Gnome | 0.8 | 0.9 | 3.2 | 1.5 |
| Kelly | 1.5 | 1.1 | 2.5 | 2.2 |
| Marquis | 0.8 | 0.5 | 3.8 | 1.5 |
| Midnight | 0.4 | 0.4 | 0.3 | 2.0 |
| Nassau | 1.1 | 2.6 | 2.4 | 0.8 |
| Ram I | 0.7 | 0.5 | 1.3 | 2.0 |
| Touchdown | 1.1 | 1.0 | 1.0 | 7.7 |
| Victa | 1.3 | 1.0 | 0.8 | 0.5 |
| LSD (.05) | 0.17 | 0.47 | 0.7 | 0.76 |

1/Degrees from the stem
2/Rating Scale: 1–9; 1 = curves up; 5 = no curve; 9 = curves down
3/Rating Scale: 0–9; 0 = none; 9 = many
4/Rating Scale: 0–9; 9 = dark purple

TABLE 7

Morphological Comparison of Peduncles, Culms, Node Numbers Per Culm and Internode Length of Ba 74-114 and Other Kentucky Bluegrass Varieties in the Greenhouse at Marysville, OH

| Variety | Peduncle Length cm | Peduncle Width mm | Culm Length cm | Nodes Per Culm | Top Internode Length cm |
|---|---|---|---|---|---|
| Ba 74-114 | 24.7 | 0.71 | 44.9 | 3.7 | 13.4 |
| Ba73-366 | 26.4 | 0.70 | 42.7 | 4.1 | 9.2 |
| Ba73-381 | 24.3 | 0.81 | 39.5 | 3.1 | 10.8 |
| Abbey | 23.2 | 0.65 | 41.3 | 4.1 | 11.0 |
| Adelphi | 24.5 | 0.66 | 40.0 | 4.0 | 10.4 |
| America | 16.2 | 0.62 | 31.8 | 3.1 | 11.0 |
| Baron | 34.0 | 0.70 | 52.8 | 4.2 | 12.8 |
| Bristol | 22.9 | 0.73 | 43.5 | 4.0 | 12.6 |
| Chateau | 20.7 | 0.61 | 38.9 | 4.4 | 9.9 |
| Coventry | 19.6 | 0.49 | 34.7 | 4.5 | 7.9 |
| Eclipse | 23.7 | 0.66 | 39.2 | 4.9 | 9.9 |
| Georgetown | 21.7 | 0.68 | 37.5 | 3.2 | 11.1 |
| Gnome | 19.4 | 0.84 | 35.3 | 3.1 | 9.2 |
| Kelly | 29.4 | 0.75 | 46.6 | 3.6 | 11.8 |
| Marquis | 27.1 | 0.83 | 34.1 | 3.4 | 7.8 |
| Midnight | 20.5 | 0.72 | 29.5 | 2.8 | 7.6 |
| Nassau | 25.0 | 0.66 | 36.0 | 3.9 | 7.4 |
| Ram I | 22.2 | 0.69 | 30.5 | 2.5 | 6.6 |
| Touchdown | 23.6 | 0.52 | 38.0 | 4.0 | 8.4 |
| Victa | 21.2 | 0.81 | 37.9 | 3.7 | 10.3 |
| LSD (.05) | 3.2 | 0.08 | 3.3 | 0.4 | 1.9 |

TABLE 8

Morphological Comparison of Vegetative Leaves of Ba 74-114 and Other Kentucky Bluegrass Varieties in the Greenhouse at Marysville, OH

| | Length | Width | Thickness | Leaf | |
|---|---|---|---|---|---|
| Variety | cm | mm | mm | Angle1/ | Curve2/ |
| Ba 74-114 | 18.9 | 4.5 | 0.36 | 50.9 | 5.0 |
| Ba73-366 | 22.9 | 3.8 | 0.40 | 53.0 | 7.1 |
| Ba73-381 | 22.1 | 3.3 | 0.30 | 62.5 | 8.2 |
| Abbey | 20.7 | 3.6 | 0.28 | 51.3 | 7.4 |
| Adelphi | 19.4 | 3.7 | 0.28 | 67.0 | 4.6 |
| America | 21.4 | 3.1 | 0.32 | 66.0 | 6.4 |
| Baron | 18.2 | 4.3 | 0.29 | 35.0 | 4.4 |
| Bristol | 18.2 | 3.7 | 0.32 | 65.5 | 6.9 |
| Chateau | 23.1 | 3.3 | 0.33 | 39.7 | 5.4 |
| Coventry | 23.4 | 3.6 | 0.25 | 63.0 | 7.3 |

TABLE 8-continued

Morphological Comparison of Vegetative Leaves of Ba 74-114 and Other Kentucky Bluegrass Varieties in the Greenhouse at Marysville, OH

| | | | | | |
|---|---|---|---|---|---|
| Eclipse | 20.3 | 4.4 | 0.30 | 65.5 | 5.4 |
| Georgetown | 19.5 | 3.6 | 0.29 | 56.7 | 5.8 |
| Gnome | 18.2 | 2.9 | 0.29 | 43.2 | 6.6 |
| Kelly | 22.8 | 3.9 | 0.30 | 55.5 | 7.0 |
| Marquis | 19.7 | 3.7 | 0.38 | 46.4 | 7.8 |
| Midnight | 19.5 | 3.5 | 0.31 | 63.3 | 5.0 |
| Nassau | 16.3 | 3.7 | 0.29 | 63.2 | 4.9 |
| Ram I | 19.1 | 3.6 | 0.27 | 70.8 | 6.5 |
| Touchdown | 16.7 | 3.7 | 0.24 | 51.3 | 4.0 |
| Victa | 21.5 | 3.6 | 0.36 | 56.3 | 6.7 |
| LSD (.05) | 3.5 | 0.43 | 0.04 | 15.9 | 1.5 |

| | Ligule | Hairs3/ | | | |
|---|---|---|---|---|---|
| Variety | Length mm | Leaf Ligule | Leaf Margin | Sheath Roughness4/ | Sheath Color5/ |
| Ba 74-114 | 0.14 | 3.3 | 2.6 | 8.7 | 2.0 |
| Ba73-366 | 0.23 | 5.2 | 4.2 | 8.5 | 0.0 |
| Ba73-381 | 0.16 | 3.2 | 0.7 | 8.2 | 2.0 |
| Abbey | 0.32 | 4.4 | 2.8 | 7.7 | 0.0 |
| Adelphi | 0.34 | 2.6 | 3.4 | 8.8 | 0.0 |
| America | 0.12 | 1.7 | 2.1 | 8.4 | 2.0 |
| Baron | 0.33 | 4.6 | 3.6 | 7.4 | 0.4 |
| Bristol | 0.12 | 2.6 | 3.0 | 8.9 | 2.0 |
| Chateau | 0.22 | 3.3 | 3.1 | 7.8 | 0.5 |
| Coventry | 0.32 | 3.1 | 2.4 | 8.1 | 0.3 |
| Eclipse | 0.38 | 2.8 | 2.6 | 9.0 | 0.2 |
| Georgetown | 0.14 | 2.5 | 2.4 | 8.5 | 2.0 |
| Gnome | 0.23 | 1.6 | 0.8 | 7.5 | 1.4 |
| Kelly | 0.34 | 4.6 | 2.4 | 8.8 | 0.0 |
| Marquis | 0.21 | 3.6 | 1.1 | 6.8 | 1.1 |
| Midnight | 0.10 | 1.3 | 1.6 | 7.7 | 2.0 |
| Nassau | 0.34 | 2.5 | 3.3 | 8.5 | 1.4 |
| Ram I | 0.09 | 1.8 | 2.0 | 7.7 | 2.0 |
| Touchdown | 0.29 | 1.4 | 1.3 | 7.9 | 8.0 |
| Victa | 0.26 | 2.3 | 1.7 | 7.9 | 0.1 |
| LSD (.05) | 0.04 | 0.79 | 0.70 | 0.89 | 0.57 |

1/Degrees from the stem
2/Rating Scale: 1–9; 1 = curves up; 5 = no curve; 9 = curves down
3/Rating Scale: 0–9; 0 = none; 9 = many
4/Rating Scale: 1–9; 1 = rough; 9 = smooth
5/Rating Scale: 0–9; 0 = no color; 9 = dark purple color Ba 74-114 has performed well throughout the U.S., as exhibited by medium to high turf quality ratings in comparison to many other Kentucky Bluegrass varieties. In addition, it has a deep dark green color which can be maintained throughout the growing season.

With regard to a comparative analysis conducted for purposes of determining color of Ba 74-114 plants relative to other Kentucky Bluegrass varieties, readings were taken of the vegetative color of Ba 74-114 during mid-May while the turf was actively growing with adequate nutrient and water availability. The readings were taken in full sun with several actively growing leaves being compared, one at a time, utilizing color chips from the Munsell Book of Color as a reference. On this basis, the color of Ba 74-114 was determined to be 7.5 GY 4/4. During the same time period, the color of similar leaves of other Kentucky Bluegrass varieties were determined by the same procedure to be as follows: Ba 73-381 — 5GY 4/4; Ba 73-366 — 5 GY 4/4; Ba 73-540 — 5 GY 4/4; Abbey — 5 GY 3/4; and Coventry — 5 GY 4/4. However, it should be noted that the general apparent color or turf does not always correlate directly with the color of the individual actively growing leaves within the turf and that turf color varies with nutrient level and time of year with some varieties being darker or lighter green depending on such factors.

Comparisons of Ba 74-114 with other Kentucky Bluegrass varieities for quality, genetic color, spring greening and winter color are set forth hereinafter in Tables 9–15:

TABLE 9

A Comparison of Quality of Ba 74-114 and Other Kentucky Bluegrass Varieties at Seven Locations in the U.S.

| | Locations[1/] | | | | | | |
|---|---|---|---|---|---|---|---|
| Variety | 1 | 2 | 3 | 4 | 5 | 6 | 7 |
| Va 74-114 | 6.4 | 7.3 | 5.4 | 5.3 | 4.9 | 5.3 | 4.9 |
| Ba73-366 | 7.2 | 5.1 | 5.3 | 4.7 | 5.0 | 5.2 | 4.7 |
| Ba73-381 | 6.9 | 5.1 | 5.4 | 4.2 | 5.3 | 4.2 | 4.1 |
| Abbey | 6.9 | 5.1 | 5.5 | 4.9 | 5.1 | 3.5 | 4.2 |
| Able I | 7.5 | 7.3 | 5.9 | 5.2 | 5.7 | 5.9 | 4.7 |
| Banff | 6.6 | 6.2 | 6.1 | 5.3 | 4.6 | 5.1 | 4.2 |
| Baron | 7.2 | 5.4 | 5.7 | 5.0 | 5.7 | 5.3 | 4.6 |
| Challenger | 6.6 | 7.3 | 4.9 | 5.9 | 5.7 | 5.7 | 4.8 |
| Classic | 6.9 | 5.5 | 6.2 | 5.5 | 4.3 | 5.6 | 4.0 |
| Coventry | 6.3 | 7.2 | 5.9 | 5.3 | 5.8 | 5.3 | 4.9 |
| Eclipse | 6.7 | 5.9 | 6.5 | 5.7 | 5.1 | 5.9 | 4.9 |
| Estate | 7.0 | 6.4 | 5.5 | 5.3 | 6.0 | 5.7 | 5.2 |
| Georgetown | 6.6 | 6.3 | 6.6 | 5.7 | 4.9 | 5.7 | 4.1 |
| Glade | 7.4 | 7.5 | 7.5 | 5.2 | 5.6 | 4.5 | 4.7 |
| Gnome | 6.8 | 5.2 | 5.0 | 5.1 | 5.0 | 4.8 | 4.7 |
| Haga | 6.7 | 5.9 | 6.3 | 5.5 | 5.1 | 5.7 | 4.1 |
| Kelly | 7.2 | 5.7 | 5.8 | 4.1 | 5.0 | 5.2 | 5.1 |
| Kenblue | 6.4 | 2.7 | 3.3 | 3.3 | 3.8 | 3.2 | 3.2 |
| Liberty | 7.0 | 6.5 | 6.0 | 4.7 | 6.0 | 5.3 | 4.2 |
| Marquis | 6.8 | 5.4 | 5.3 | 5.1 | 5.5 | 4.7 | 5.0 |
| Merion | 5.1 | 2.7 | 2.7 | 4.0 | 4.2 | 4.8 | 4.7 |
| Merit | 6.9 | 4.8 | 4.9 | 4.5 | 4.1 | 4.9 | 4.7 |
| Midnight | 7.1 | 7.9 | 8.3 | 6.6 | 4.7 | 5.7 | 4.6 |
| Monopoly | 6.5 | 4.9 | 5.0 | 4.3 | 4.8 | 5.1 | 3.9 |
| Nassau | 6.9 | 5.8 | 6.4 | 4.5 | 5.5 | 5.5 | 3.9 |
| Ram I | 7.8 | 7.3 | 6.0 | 5.7 | 5.2 | 5.2 | 4.7 |
| South Dakota | 6.6 | 4.3 | 3.0 | 2.2 | 2.1 | 2.7 | 3.3 |
| Touchdown | 7.2 | 7.1 | 4.2 | 5.2 | 3.3 | 5.1 | 4.8 |
| LSD (.05) | 0.8 | 1.1 | 0.9 | 1.0 | 1.1 | 0.5 | 0.7 |

Rating Scale: 1–0; 9 = ideal turf

[1/]Locations: 1 — Ames, IA; 2 — Post Falls, ID; 3 — Adelphia NJ; 4 — Martinsville, NJ; 5 — Hubbard, OR; 6 — pooled data from Halsey, Hubbard and Gervais, OR; 7 — Haymarket, VA.

TABLE 10

A Comparison of Quality of Ba 74-114 and Other Kentucky Bluegrass Varieties Grown in the Shade in Four Tests (A–D) Conducted at Marysville, OH

| | Quality Tests | | | |
|---|---|---|---|---|
| Variety | A | B | C | D |
| Ba 74-114 | 3.0 | 2.7 | 2.5 | 3.0 |
| Adelphi | 2.5 | 3.2 | 2.8 | 2.8 |
| Bonnieblue | 2.6 | 2.4 | 2.4 | 1.8 |
| Bristol | 3.0 | 2.6 | 2.7 | 2.9 |
| Fylking | 1.9 | 2.0 | 2.3 | 2.5 |
| Merion | 2.4 | 2.5 | 2.3 | 1.8 |
| Merit | 1.4 | 1.9 | 2.2 | 1.9 |
| Newport | 2.4 | 2.2 | 2.2 | 2.3 |
| Nugget | 2.2 | 2.6 | 2.5 | 2.3 |
| Park | 1.7 | 2.0 | 2.2 | 1.9 |
| Pennstar | 1.2 | 1.8 | 2.2 | 1.8 |
| Victa | 1.3 | 1.5 | 1.8 | 1.8 |
| Mean | 2.1 | 2.0 | 2.0 | 2.1 |
| LSD (.05) | 0.7 | 0.7 | 0.6 | 0.7 |

Rating Scale: 1–5; 5 = ideal turf

TABLE 11

A Comparison of Quality of Ba 74-114 and Other Kentucky Bluegrass Varieties Grown under Shade Conditions in Five Tests (A–E) Conducted at Marysville, OH

| | Qualily Tests | | | | |
|---|---|---|---|---|---|
| Variety | A | B | C | D | E |
| Ba 74-114 | 2.1 | 2.5 | 1.9 | 2.1 | 7.0 |
| Ba73-366 | 1.5 | 1.0 | 1.6 | 1.5 | 6.0 |
| Ba73-381 | 1.8 | 2.3 | 1.7 | 1.6 | 6.5 |
| Adelphi | 1.5 | 2.5 | 1.8 | 1.6 | 7.5 |
| Bristol | 1.5 | 1.8 | 1.6 | 2.0 | 6.0 |
| Dormie | 1.5 | 3.0 | 1.9 | 1.7 | 5.5 |
| Glade | 1.5 | 1.4 | 1.7 | 2.0 | 6.0 |
| Merion | 1.8 | 1.5 | 1.4 | 1.5 | 5.5 |
| Monopoly | 1.8 | 3.0 | 1.9 | 2.2 | 7.0 |
| Nassau | 1.6 | 2.2 | 1.8 | 1.7 | 6.5 |
| Park | 1.5 | 2.0 | 1.8 | 1.7 | 6.0 |
| Ram I | 1.8 | 2.2 | 1.7 | 1.6 | 6.0 |
| Vantage | 1.6 | 2.8 | 1.8 | 2.0 | 6.5 |
| Victa | 1.7 | 1.3 | 1.6 | 1.3 | 6.0 |
| Wabash | 1.6 | 2.8 | 1.8 | 2.3 | 5.5 |
| Mean | 1.6 | 2.2 | 1.7 | 1.7 | 6.3 |
| LSD (.05) | 0.44 | 1.2 | 0.34 | 0.39 | 1.2 |

Rating Scale for Tests A–D: 1–5; 5 = best
Rating Scale for Test E: 1–9; 9 = best

TABLE 12

A Comparison of Genetic Color of Ba 74-114 and Other Kentucky Bluegrass Varieties in Three Tests (A–C) Conducted at Ten (10) Locations in the US

| | TESTS (Annual Means) | | |
|---|---|---|---|
| Variety | A | B | C |
| Ba 74-114 | 7.0 | 7.2 | 7.2 |
| Ba73-366 | 5.5 | 5.5 | 5.9 |
| Ba73-381 | 6.0 | 5.7 | 6.4 |
| Abbey | 5.6 | 5.9 | 5.8 |
| Able I | 6.6 | 6.8 | 6.8 |
| A-34 | 5.0 | 5.4 | 4.6 |
| Banff | 5.1 | 6.0 | 5.5 |
| Baron | 6.0 | 6.0 | 5.9 |
| Classic | 5.2 | 5.9 | 5.2 |
| Coventry | 5.9 | 5.6 | 5.8 |
| Eclipse | 6.3 | 6.6 | 6.4 |
| Estate | 5.8 | 5.3 | 5.3 |
| Georgetown | 5.2 | 6.1 | 5.3 |
| Glade | 6.7 | 6.3 | 6.7 |
| Gnome | 6.0 | 6.1 | 5.8 |
| Haga | 5.1 | 5.8 | 5.3 |
| Kelly | 5.6 | 5.7 | 6.1 |
| Kenblue | 4.6 | 5.0 | 5.3 |
| Marquis | 6.1 | 6.1 | 6.4 |
| Merion | 5.7 | 5.8 | 5.4 |
| Merit | 5.7 | 5.7 | 6.2 |
| Midnight | 7.1 | 7.3 | 7.7 |
| Monopoly | 4.8 | 4.9 | 4.8 |
| Nassau | 6.0 | 6.6 | 6.5 |
| Ram I | 6.7 | 5.9 | 6.6 |
| South Dakota | 4.5 | 4.8 | 4.7 |
| Touchdown | 5.5 | 5.5 | 5.3 |
| LSD (.05) | 0.5 | 0.4 | 0.7 |

Rating Scale: 1–9; 9 = dark green.

TABLE 13

A Comparison of Spring Greenup for Ba 74-114 and Other Kentucky Bluegrass Varieties at Two Locations

| Variety | Spring Greenup: North Brunswick, NJ | Spring Greenup: Martinsville, NJ | Spring Greenup: Mean |
|---|---|---|---|
| Ba 74-114 | 7.0 | 5.7 | 6.3 |
| Ba73-366 | 4.0 | 5.0 | 4.5 |
| Ba73-381 | 3.3 | 4.0 | 3.7 |
| Abbey | 3.7 | 5.7 | 4.7 |
| Able I | 3.7 | 6.7 | 5.2 |
| A-34 | 4.7 | 6.0 | 5.3 |
| Banff | 5.0 | 5.3 | 5.2 |
| Baron | 2.3 | 5.3 | 3.8 |
| Classic | 6.0 | 5.7 | 5.8 |
| Coventry | 2.7 | 5.3 | 4.0 |
| Eclipse | 5.3 | 5.0 | 5.2 |
| Estate | 2.7 | 5.3 | 4.0 |
| Georgetown | 4.7 | 4.7 | 4.7 |
| Glade | 3.3 | 6.7 | 5.0 |
| Gnome | 3.3 | 6.3 | 4.8 |
| Haga | 4.0 | 5.3 | 4.7 |
| Kelly | 3.7 | 6.0 | 4.8 |
| Kenblue | 4.0 | 5.0 | 4.5 |
| Liberty | 5.3 | 5.3 | 5.3 |
| Marquis | 3.0 | 5.7 | 4.3 |
| Merion | 6.3 | 6.3 | 6.3 |
| Merit | 3.3 | 6.7 | 5.0 |
| Midnight | 3.3 | 6.0 | 4.7 |
| Monopoly | 4.0 | 6.7 | 5.3 |
| Nassau | 6.3 | 5.0 | 5.7 |
| Ram I | 5.0 | 7.0 | 6.0 |
| South Dakota | 5.3 | 3.7 | 4.5 |
| Touchdown | 5.3 | 7.0 | 6.2 |
| LSD (.05) | 1.2 | 1.5 | 0.9 |

Rating Scale: 1–9; 9 = completely green

TABLE 14

A Comparison of Spring Greenup for Ba 74-114 and Other Kentucky Bluegrass Varieties at Marysville, OH

| Variety | Spring Greenup |
|---|---|
| Ba 74-114 | 4.7 |
| Ba73-366 | 3.0 |
| Ba73-381 | 3.3 |
| Banff | 4.0 |
| Baron | 3.5 |
| Bristol | 4.3 |
| Classic | 3.0 |
| Eclipse | 4.3 |
| Georgetown | 4.0 |
| Glade | 3.3 |
| Kenblue | 4.0 |
| Merion | 4.7 |
| Merit | 3.7 |
| Nassau | 4.0 |
| Newport | 4.0 |
| Park | 3.0 |
| Ram I | 3.0 |
| Vantage | 4.3 |
| Victa | 3.3 |
| LSD (.05) | 1.0 |

Rating scale: 1–9; 9 = completely green

TABLE 15

A Comparison of Winter Color of Ba 74-114 and Other Kentucky Bluegrass Varieties at Two Locations in the U.S.

| Variety | Locations[1/]: 1 | Locations[1/]: 2 | Mean |
|---|---|---|---|
| Ba 74-114 | 2.7 | 7.0 | 4.8 |
| Ba73-366 | 3.0 | 5.7 | 4.3 |
| Ba73-381 | 2.7 | 2.7 | 2.7 |
| Abbey | 3.3 | 5.7 | 4.5 |
| Able I | 4.0 | 7.0 | 5.5 |
| A-34 | 4.0 | 4.3 | 4.2 |
| Banff | 4.0 | 5.0 | 4.5 |
| Baron | 3.7 | 3.7 | 3.7 |
| Classic | 4.0 | 5.7 | 4.8 |
| Coventry | 2.7 | 4.3 | 3.5 |
| Eclipse | 3.3 | 5.7 | 4.5 |
| Estate | 3.7 | 5.3 | 4.5 |
| Georgetown | 4.7 | 7.0 | 5.8 |
| Glade | 2.7 | 4.7 | 3.7 |
| Gnome | 2.7 | 4.3 | 3.5 |
| Haga | 3.3 | 5.3 | 4.3 |
| Kelly | 3.0 | 5.3 | 4.2 |
| Kenblue | 3.3 | 2.7 | 3.0 |
| Liberty | 3.3 | 6.3 | 4.8 |
| Marquis | 3.3 | 4.0 | 3.7 |
| Merion | 2.3 | 6.3 | 4.3 |
| Merit | 3.3 | 5.3 | 4.3 |
| Midnight | 3.3 | 5.3 | 4.3 |
| Monopoly | 3.3 | 5.0 | 4.2 |
| Nassau | 3.0 | 5.7 | 4.3 |
| Ram I | 3.7 | 6.0 | 4.8 |
| South Dakota | 1.7 | 2.0 | 1.8 |
| Touchdown | 3.3 | 5.3 | 4.3 |
| LSD (.05) | 1.0 | 1.6 | 0.9 |

Rating Scale: 1–9; 9 = complete color retention

[1/]Locations: 1 Martinsville, N.J.; 2 pooled data from Halsey, Hubbard and Gervais, OR.

Further comparisons of Ba 74-114 with other Kentucky Bluegrass varieties for leaf texture and height of growth are set forth in Tables 16–17 as follows:

TABLE 16

A Comparison of Leaf Texture of Ba 74-114 and Other Kentucky Bluegrass Varieties at Martinsville, NJ.

| Variety | Leaf Texture |
|---|---|
| Ba 74-114 | 4.0 |
| Ba73-366 | 4.3 |
| Ba73-381 | 4.0 |
| Abbey | 5.0 |
| Able I | 5.7 |
| A-34 | 4.3 |
| Banff | 5.3 |
| Baron | 5.0 |
| Classic | 5.3 |
| Coventry | 5.0 |
| Eclipse | 5.7 |
| Estate | 4.3 |
| Georgetown | 6.0 |
| Glade | 5.0 |
| Gnome | 5.3 |
| Haga | 5.7 |
| Kelly | 4.3 |
| Kenblue | 6.0 |
| Liberty | 5.0 |
| Marquis | 4.3 |
| Merion | 4.0 |
| Merit | 4.7 |
| Midnight | 6.7 |
| Monopoly | 5.0 |
| Nassau | 5.0 |

TABLE 16-continued

A Comparison of Leaf Texture of Ba 74-114 and Other Kentucky Bluegrass Varieties at Martinsville, NJ.

| Variety | Leaf Texture |
|---|---|
| Ram I | 5.0 |
| South Dakota | 3.7 |
| Touchdown | 5.3 |

Rating Scale: 1–9; 9 = very fine

TABLE 17

A Comparison of Height (in millimeters) One Week after Mowing under Lawn Conditions of Ba 74-114 and Other Kentucky Bluegrass Varieties at Marysville, OH.

| Variety | Height (mm) |
|---|---|
| Ba 74-114 | 109.5 |
| Adelphi | 115.0 |
| Baron | 194.3 |
| Bonnieblue | 145.0 |
| Bristol | 101.3 |
| Fylking | 133.0 |
| Kenblue | 140.3 |
| Merion | 106.7 |
| Newport | 135.3 |
| Nugget | 120.3 |
| Park | 124.7 |
| Pennstar | 118.3 |
| Vantage | 131.3 |
| Victa | 115.7 |
| LSD | 24.6 |

Turf diseases are one of the major causes of inconsistent and poor turf performance. Ba 74-114 has been found to have a medium to high level of resistance to the following diseases: (1) leaf spot and melting out caused by *Drechslera poae* (formerly called *Helminthosporium vagans*); (2) dollar spot caused by *Sclerotinia homoecarpa;* (3) several rust diseases causes by Puccinia spp.; (4) stripe smut caused by *Ustilago striiformis;* and (5) powdery mildew caused by *Erysiphe graminis.*

Comparisons of disease incidence of Ba 74-114 as compared with other Kentucky Bluegrass varieties in regard to leaf spot, dollar spot, rusts, stripe smut and powdery mildew are presented in Tables 18–26. An additional comparison is presented in Table 27 for seed yields.

TABLE 18

A Comparison of Leaf Spot Disease Incidence in Ba 74-114 and Other Kentucky Bluegrass Varieties in Tests Conducted at Three Locations in the U.S.[1/]

| Variety | Mean |
|---|---|
| Ba 74-114 | 4.7 |
| Ba73-366 | 4.3 |
| Ba73-381 | 2.0 |
| Abbey | 4.7 |
| Able I | 6.0 |
| A-34 | 4.7 |
| Banff | 4.7 |
| Baron | 4.0 |
| Classic | 3.3 |
| Coventry | 3.7 |
| Eclipse | 6.3 |
| Estate | 4.0 |
| Georgetown | 6.0 |
| Glade | 3.0 |
| Gnome | 3.7 |

TABLE 18-continued

A Comparison of Leaf Spot Disease Incidence in Ba 74-114 and Other Kentucky Bluegrass Varieties in Tests Conducted at Three Locations in the U.S.[1/]

| Variety | Mean |
|---|---|
| Haga | 3.7 |
| Kelly | 4.7 |
| Kenblue | 1.7 |
| Liberty | 5.7 |
| Marquis | 3.7 |
| Merion | 7.3 |
| Merit | 4.3 |
| Midnight | 5.7 |
| Monopoly | 4.3 |
| Nassau | 4.3 |
| Ram I | 4.3 |
| South Dakota | 1.0 |
| Touchdown | 5.3 |
| LSD (.05) | 1.5 |

Rating Scale: 1–9; 9 = no disease

[1/]Locations: Pooled data from Halsey, Hubbard and Gervais, OR.

TABLE 19

A Comparison of Leaf Spot Disease Incidence in Ba 74-114 and Other Kentucky Bluegrass Varieties in Tests Conducted at Marysville, OH

| Variety | % Leaf Spot |
|---|---|
| Ba 74-114 | 10.0 |
| Adelphi | 33.3 |
| Baron | 26.7 |
| Bonnieblue | 10.0 |
| Bristol | 16.7 |
| Kenblue | 76.7 |
| Merion | 23.3 |
| Newport | 50.0 |
| Park | 73.3 |
| Pennstar | 13.3 |
| Vantage | 40.0 |
| Victa | 26.7 |
| LSD (.05) | 18.7 |

TABLE 20

A Comparison of Leaf Spot Disease Incidence in Ba 74-114 and Other Kentucky Bluegrass Varieties Grown under Shade Conditions at Marysville, OH

| Variety | % Leaf Spot |
|---|---|
| Ba 74-114 | 0.0 |
| Ba73-366 | 0.0 |
| Ba73-381 | 0.0 |
| America | 40.0 |
| Banff | 2.5 |
| Bristol | 0.0 |
| Classic | 5.0 |
| Eclipse | 2.5 |
| Georgetown | 7.5 |
| Glade | 7.5 |
| Kenblue | 10.0 |
| Merion | 0.0 |
| Merit | 0.0 |
| Nassau | 0.0 |
| Newport | 0.0 |
| Park | 50.0 |
| Ram I | 40.0 |
| Sydsport | 27.5 |
| Vantage | 2.5 |
| Victa | 2.5 |
| LSD (.05) | 26.7 |

TABLE 21

A Comparison of Dollar Spot Disease Incidence of Ba 74-114 and Other Kentucky Bluegrass Varieties at Kingston, R.I.

| Variety | Dollar Spot |
|---|---|
| Ba 74-114 | 8.3 |
| Ba73-366 | 8.3 |
| Ba73-381 | 7.3 |
| Abbey | 8.0 |
| Able I | 8.3 |
| A-34 | 7.7 |
| Banff | 7.7 |
| Baron | 7.7 |
| Classic | 8.0 |
| Coventry | 7.7 |
| Eclipse | 8.3 |
| Estate | 8.3 |
| Georgetown | 8.0 |
| Glade | 7.7 |
| Gnome | 8.0 |
| Haga | 7.7 |
| Kelly | 8.0 |
| Kenblue | 8.0 |
| Liberty | 8.0 |
| Marquis | 8.0 |
| Merion | 7.7 |
| Merit | 8.0 |
| Midnight | 8.3 |
| Monopoly | 8.0 |
| Nassau | 8.0 |
| Ram I | 7.3 |
| South Dakota | 8.0 |
| Touchdown | 8.0 |
| LSD (.05) | 0.9 |

Rating Scale: 1–9; 9 = no disease

TABLE 22

A Comparison of Dollar Spot Disease Incidence in Ba 74-114 and Other Kentucky Bluegrass Varieties at Marysville, OH

| Variety | % Dollar Spot |
|---|---|
| Ba 74-114 | 0.0 |
| Baron | 20.7 |
| Bonnieblue | 0.0 |
| Bristol | 0.0 |
| Kenblue | 3.3 |
| Merion | 20.0 |
| Newport | 0.3 |
| Nugget | 26.0 |
| Park | 0.0 |
| Pennstar | 0.7 |
| Vantage | 0.3 |
| Victa | 1.7 |
| LSD (.05) | 13.9 |

TABLE 23

A comparison of Powdery Mildew Disease Incidence in Ba 74-114 and Other Kentucky Bluegrass Varieties Grown under Shade Conditions in Three Tests (A–C) Conducted at Marysville, OH

| | % Powdery Mildew | | | |
|---|---|---|---|---|
| Variety | A | B | C | Mean |
| Ba 74-114 | 0.0 | 10.0 | 0.0 | 3.3 |
| Ba73-366 | 30.0 | 72.5 | 80.0 | 60.8 |
| Ba73-381 | 67.5 | 90.0 | 70.0 | 75.8 |
| Banff | 0.0 | 0.0 | 15.0 | 5.0 |
| Bristol | 5.0 | 12.5 | 0.6 | 5.8 |
| Classic | 27.5 | 60.0 | 75.0 | 54.2 |
| Eclipse | 0.0 | 5.0 | 0.0 | 1.7 |

TABLE 23-continued

A comparison of Powdery Mildew Disease Incidence in Ba 74-114 and Other Kentucky Bluegrass Varieties Grown under Shade Conditions in Three Tests (A–C) Conducted at Marysville, OH

| | % Powdery Mildew | | | |
|---|---|---|---|---|
| Variety | A | B | C | Mean |
| Georgetown | 7.5 | 30.0 | 0.0 | 12.5 |
| Glade | 50.0 | 45.0 | 25.0 | 40.0 |
| Kenblue | 0.0 | 10.0 | 0.0 | 3.3 |
| Merion | 35.0 | 37.5 | 40.0 | 37.5 |
| Merit | 50.0 | 65.0 | 85.0 | 66.7 |
| Nassau | 32.5 | 40.0 | 0.0 | 24.2 |
| Newport | 20.0 | 25.0 | 15.0 | 20.0 |
| Park | 0.0 | 2.5 | 0.0 | 0.8 |
| Ram I | 20.0 | 17.5 | 0.0 | 12.5 |
| Vantage | 0.0 | 22.5 | 15.0 | 12.5 |
| Victa | 50.0 | 50.0 | 70.0 | 56.7 |
| Mean | 20.3 | 32.6 | 26.4 | 26.4 |
| LSD (.05) | 33.9 | 29.6 | 49.3 | |

TABLE 24

A Comparison of Leaf Rust Disease Incidence in Ba 74-114 and Other Kentucky Bluegrass Varieties at Kingston, R.I.

| Variety | Leaf Rust |
|---|---|
| Ba 74-114 | 6.7 |
| Ba73-366 | 5.7 |
| Ba73-381 | 6.3 |
| Abbey | 6.3 |
| Abel I | 7.0 |
| A-34 | 6.0 |
| Banff | 7.0 |
| Baron | 8.3 |
| Classic | 8.7 |
| Coventry | 7.0 |
| Eclipse | 5.7 |
| Estate | 6.3 |
| Georgetown | 7.7 |
| Glade | 7.0 |
| Gnome | 6.7 |
| Haga | 7.0 |
| Kelly | 5.0 |
| Kenblue | 6.7 |
| Liberty | 7.3 |
| Marquis | 6.3 |
| Merion | 2.3 |
| Merit | 6.0 |
| Midnight | 6.0 |
| Monopoly | 5.3 |
| Nassau | 7.0 |
| Ram I | 6.7 |
| South Dakota | 6.7 |
| Touchdown | 3.7 |
| LSD (.05) | 2.4 |

Rating Scale: 1–9; 9 = no disease

TABLE 25

A Comparison of Stripe Rust Disease Incidence in Ba 74-114 and Other Kentucky Bluegrass Varieties in Tests Conducted at Three Locations[1/] in Oregon 1991.

| Variety | Stripe Rust |
|---|---|
| Ba 74-114 | 5.7 |
| Ba73-366 | 5.0 |
| Ba73-381 | 4.7 |
| Abbey | 4.3 |
| Able I | 6.0 |
| A-34 | 5.0 |

TABLE 25-continued

A Comparison of Stripe Rust Disease Incidence in Ba 74-114 and Other Kentucky Bluegrass Varieties in Tests Conducted at Three Locations[1/] in Oregon 1991.

| Variety | Stripe Rust |
|---|---|
| Banff | 6.0 |
| Baron | 6.0 |
| Classic | 6.3 |
| Coventry | 5.0 |
| Eclipse | 6.0 |
| Estate | 5.7 |
| Georgetown | 6.3 |
| Glade | 3.0 |
| Gnome | 4.7 |
| Haga | 6.3 |
| Kelly | 5.0 |
| Kenblue | 3.3 |
| Liberty | 5.3 |
| Marquis | 5.3 |
| Merion | 3.7 |
| Merit | 5.0 |
| Midnight | 4.7 |
| Monopoly | 5.3 |
| Nassau | 5.3 |
| Ram I | 6.0 |
| South Dakota | 4.0 |
| Touchdown | 3.0 |
| LSD (.05) | 1.2 |

Rating Scale: 1–9; 9 = no disease
[1/]Pooled data from Halsey, Hubbard and Gervais, Oregon.

TABLE 26

A Comparison of Stripe Smut Disease Incidence in Ba 74-114 and Other Kentucky Bluegrass Varieties at Marysville, OH.

| Variety | Stripe Smut |
|---|---|
| Ba 74-114 | 8.0 |
| Ba73-366 | 6.3 |
| Ba73-381 | 7.0 |
| America | 6.7 |
| Banff | 8.0 |
| Baron | 8.0 |
| Bonnieblue | 8.0 |
| Bristol | 7.7 |
| Classic | 8.0 |
| Eclipse | 7.3 |
| Georgetown | 7.7 |

TABLE 26-continued

A Comparison of Stripe Smut Disease Incidence in Ba 74-114 and Other Kentucky Bluegrass Varieties at Marysville, OH.

| Variety | Stripe Smut |
|---|---|
| Glade | 7.7 |
| Kelly | 6.3 |
| Kenblue | 7.0 |
| Merion | 7.7 |
| Merit | 5.7 |
| Nassau | 7.7 |
| Newport | 7.3 |
| Park | 6.7 |
| Ram I | 7.3 |
| Vantage | 7.3 |
| victa | 5.0 |
| LSD (.05) | 1.2 |

Rating Scale: 1–9; 9 = least disease

TABLE 27

A Comparison of Seed Yields of Ba 74-114 and Other Kentucky Bluegrass Varieties at Gervais, Oregon.

| Variety | Lbs/Acre |
|---|---|
| Ba 74-114 | 427 |
| Abbey | 919 |
| Georgetown | 654 |
| Gnome | 706 |
| Marquis | 900 |
| LSD (.05) | 248 |

What is claimed is:

1. A variety of Kentucky Bluegrass plant, substantially as shown and described, characterized by a medium to high level of resistance to a broad spectrum of serious diseases, including leaf spot and melting out disease, dollar spot, rusts, stripe smut and powdery mildew; a dark green color throughout the growing season; medium to high quality turf formation under a wide variety of environmental conditions; a moderately wide blade; a low growth habit; and a medium level of seed yielding capacity.

* * * * *